(12) United States Patent
Yamagami

(10) Patent No.: US 6,611,577 B1
(45) Date of Patent: Aug. 26, 2003

(54) X-RAY FLUORESCENCE ANALYSIS AND APPARATUS THEREFOR

(75) Inventor: Motoyuki Yamagami, Takatsuki (JP)

(73) Assignee: Rigaku Industrial Corporation, Takatsuki (JP)

( * ) Notice: Subject to any disclaimer, the term of this patent is extended or adjusted under 35 U.S.C. 154(b) by 0 days.

(21) Appl. No.: 10/068,953

(22) Filed: Feb. 11, 2002

(51) Int. Cl.⁷ .............................................. G01N 23/223
(52) U.S. Cl. .......................... 378/48; 378/45; 378/50; 378/207
(58) Field of Search ............................. 378/44, 45, 46, 378/48, 49, 50, 207

(56) References Cited

U.S. PATENT DOCUMENTS

| | | | | |
|---|---|---|---|---|
| 5,249,216 A | * | 9/1993 | Ohsugi et al. ................. | 378/46 |
| 5,686,314 A | * | 11/1997 | Miyazaki ..................... | 436/177 |
| 5,742,658 A | * | 4/1998 | Tiffin et al. .................... | 378/44 |
| 5,754,620 A | * | 5/1998 | Hossain et al. ................ | 378/45 |
| 5,841,016 A | * | 11/1998 | Hossain et al. ................ | 73/1.01 |
| 6,041,096 A | * | 3/2000 | Doi et al. ...................... | 378/48 |
| 6,043,486 A | * | 3/2000 | Hossain ..................... | 250/252.1 |
| 6,173,036 B1 | * | 1/2001 | Hossain et al. ................ | 378/45 |
| 6,381,303 B1 | * | 4/2002 | Vu et al. ....................... | 378/46 |
| 6,389,102 B2 | * | 5/2002 | Mazor et al. .................. | 378/89 |

* cited by examiner

Primary Examiner—Drew A. Dunn
Assistant Examiner—Allen C. Ho

(57) ABSTRACT

In order to render the value of the fluorescent X-ray strength Ia2 of a standard sample 2 multiplied by the ratio PF1/PF2 between respective grading coefficients of standard samples 1 and 2 to approach the value of the fluorescent X-ray strength Ia1 of the standard sample 1, specific glancing angles øa* and øb* are determined. The abundance of a substance of interest is determined from fluorescent X-ray strengths Ia3 and Ib3 of a sample to be measured that is irradiated at the determined specific glancing angles øa* and øb*, to thereby provide an accurate determination of the abundance of the substance of interest.

14 Claims, 4 Drawing Sheets

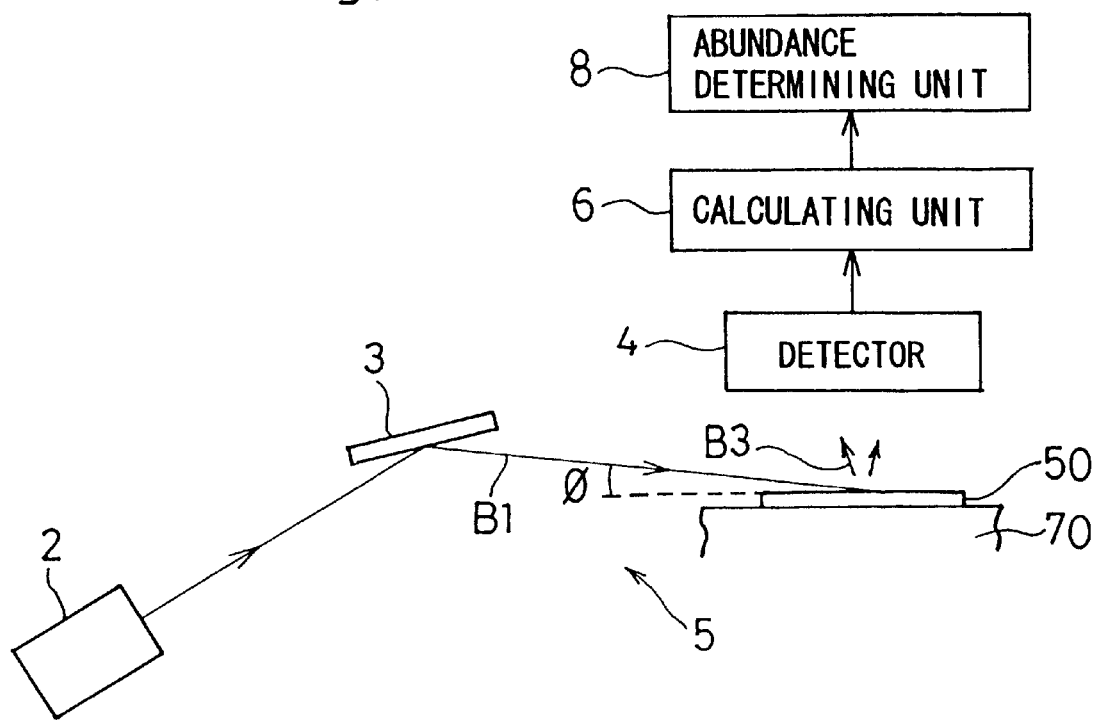

X-RAY FLUORESCENCE ANALYSIS AND APPARATUS THEREFOR

BACKGROUND OF THE INVENTION

1. Field of the Invention

The present invention relates to a X-ray fluorescence analysis and an X-ray fluorescence spectrometer for analyzing fluorescent X-rays emitted from a substance of interest present on a surface of a sample to be analyzed such as, for example, a silicon substrate.

2. Description of the Prior Art

For the determination of the identity and/or the abundance of at least one contaminant that is a substance of interest deposited on a surface of, for example, a silicon substrate, the total reflection X-ray fluorescence analysis has long been employed. In order to analyze a contaminant of a transition metal, particularly iron, nickel, copper or zinc of a kind found in the vicinity of the surface of the silicon substrate as a substance of interest, the use has been made of, for example, W-Lβ lines as primary X-rays. Such lines are projected so as to be incident upon the surface of the silicon substrate at a minute angle of incidence so that the identity of such transition metal can be determined in terms of the quantity of energies of the fluorescent X-rays emitted from the substance of interest and the abundance of such transit metal can be determined in terms of the strength of the fluorescent X-rays emitted from the substance of interest.

However, the substance of interest, of which the identity and/or the abundance are to be determined, is deposited in various ways or distribution manners on the surface of the silicon substrate having an oxide film formed thereon. For example, the substance of interest may be distributed in the form of a film on the oxide film of $SiO_2$ as shown in FIG. 4A, in the form of grains on the oxide film of $SiO_2$ as shown in FIG. 4B, or in the form as distributed randomly within the oxide film of $SiO_2$ and/or at the interface between the oxide film of $SiO_2$ and the substrate of Si as shown in FIG. 4C. Accordingly, even though the abundance of the substance of interest remains the same, measurement of the strength of the fluorescent X-rays emitted as a result of excitation by the predetermined primary X-ray varies depending on the manner of distribution of the substance of interest. For this reason, the abundance of the substance of interest calculated on the basis of the measured strength of the fluorescent X-rays varies as well depending on the manner of distribution of the substance of interest and, therefore, the total reflection X-ray fluorescence analysis is incapable of giving an accurate abundance of the substance of interest.

SUMMARY OF THE INVENTION

Accordingly, the present invention has been devised with a view to substantially eliminating the above discussed problems and is intended to provide a fluorescent X-ray analyzing method and a X-ray fluorescence spectrometer capable of accurately measuring the abundance of the substance of interest present in a sample to be analyzed.

In order to accomplish the foregoing object of the present invention, there is provided a fluorescent X-ray analyzing method for measuring fluorescent X-rays emitted from a substance of interest present on a surface area of a sample by irradiating the surface area of the sample with primary X-rays. This X-ray analyzing method includes measurement of a strength of fluorescent X-rays by projecting the primary X-rays onto standard samples 1 and 2 having different distribution of the substance of interest, but having the same abundance of the substance of interest, so as to impinge thereupon at a plurality of different glancing angles of ø1 to øn.

Then, using two glancing angles øa and øb (where øa<øb) arbitrarily chosen from the plural glancing angles, a ratio between the strengths Ia1 and Ib1 of the fluorescent X-rays, emitted from the standard sample 1 when irradiated at respective angles øa and øb, is determined as a grading coefficient PF1 of the standard sample 1 and a ratio between the strengths Ia2 and Ib2 of the fluorescent X-rays, emitted from the standard sample 2 when irradiated at angles øa and øb, is determined as a grading coefficient PF2 of the standard sample 2. In the present invention, the ratio of the strengths of the fluorescent X-rays emitted from a single substance of interest determined at those two glancing angles is defined as a grading coefficient PF. The grading coefficient PF so defined represents distribution of the substance of interest.

Thereafter, in order to render the value of Ia2·PF1/PF2 to approach the value of Ia1, or to render the ratio Ia1/Ia2 to approach the ratio PF1/PF2 between the determined grading coefficients of the standard samples 1 and 2, the specific glancing angles øa* and øb* are determined and the abundance of the substance of interest is determined from the respective strengths Ia3 and Ib3 of the fluorescent X-rays of a sample to be measured that is irradiated at the determined specific glancing angles øa* and øb*.

The X-ray fluorescence spectrometer of the present invention disclosed herein is for measuring fluorescent X-rays emitted from a substance of interest present on a surface area of a sample by irradiating the surface area of the sample with primary X-rays. This fluorescence spectrometer includes a measuring unit for measuring a strength of fluorescent X-rays by projecting the primary X-rays onto standard samples 1 and 2 having different distribution of the substance of interest, but having the same abundance of the substance of interest, so as to impinge thereupon at a plurality of different glancing angles of ø1 to øn. The fluorescence spectrometer further includes a calculating means for determining a ratio between the strengths Ia1 and Ib1 of the fluorescent X-rays, emitted from the standard sample 1, for two glancing angles øa and øb (where øa<øb) arbitrarily chosen from the plural glancing angles, as a grading coefficient PF1 of the standard sample 1, and also determining a ratio between the strength Ia2 and Ib2 of the fluorescent X-rays, emitted from the standard sample 2, for those two glancing angles øa andøb, as a grading coefficient PF2 of the standard sample 2, and then determining the corresponding specific glancing angles øa* and øb* (øa*<øb*) at which the ratio of Ia2·PF1/PF2 can take a value approximating to Ia1; and an abundance determining unit for determining the abundance of the substance of interest from strengths Ia3 and Ib3 of the fluorescent X-rays emitted from a sample to be measured when the latter is irradiated with the primary X-rays at respective glancing angles øa* and øb* so determined.

According to the present invention, since the specific glancing angles øa* and øb* are so determined that the value of the fluorescent X-ray strength Ia2 of the standard sample 2 multiplied by the ratio PF1/PF2 between the respective grading coefficients of the standard samples 1 and 2 can approach the value of the fluorescent X-ray strength Ia1 of the standard sample 1 and the abundance of the substance of interest is then determined based on the fluorescent X-ray strengths Ia3 and Ib3 given by the sample to be measured that is irradiated at the determined specific glancing angles øa* and øb*, the abundance of the substance of interest can be accurately determined regardless of the distribution thereof. The specific glancing angles øa* and øb* are chosen to be so minute as to suite for total reflection at the surface of area of the sample to be measured.

In the practice of the present invention, a status in that the value of Ia2·PF1/PF2 approaches the value of Ia1 means that the coefficient A represented by (Ia2/Ia1)·(PF1/PF2) approaches 1. As the coefficient A approaches 1, it is possible to highly accurately determine the abundance of the substance of interest. The coefficient A may be within the range of 0.3 to 3, preferably within the range of 0.4 to 2.5, particularly preferably within the range of 0.7 to 1.5, and more preferably within the range of 0.8 to 1.2.

Preferably, the manner in which the substance of interest is distributed is determined based on the ratio or difference between strengths of the fluorescent X-rays emitted from the sample that is irradiated with the primary X-rays at at least two glancing angles.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 1 is a schematic side view of an X-ray fluorescence spectrometer according to a preferred embodiment of the present invention;

DETAILED DESCRIPTION OF THE EMBODIMENTS

Figure 2A:
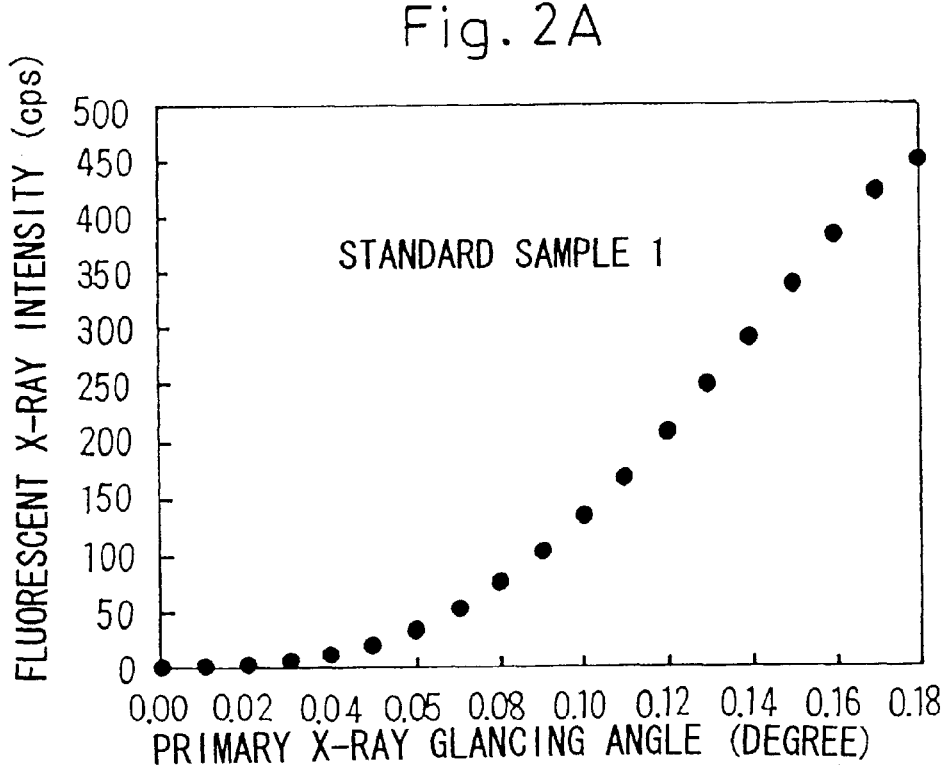
FIG. 2A is a characteristic chart showing the relationship between the strength of the fluorescent X-rays and the angle of irradiation of the primary X-rays, which is applicable where the substance of interest is distributed in the form of a film.

Referring to FIG. 1, there is shown, in a schematic side representation, a total reflection X-ray fluorescence spectrometer according to a preferred embodiment of the present invention. The illustrated X-ray fluorescence spectrometer includes an X-ray source 2 for emitting X-rays, a spectroscopic device or monochromator 3 for diffracting X-rays, emitted from the X-ray source 2, to provide monochromatic primary X-rays B1 that are subsequently projected towards a sample 50 such as, for example, a silicon substrate, placed on a sample table 70, so as to be incident upon a surface of the sample 50 at an minute incident angle of, for example, 0.05 to 0.2 degree, and a detector 4 positioned so as to confront the surface of the sample 50 for detecting fluorescent X-rays B3 emitted from the sample 50 as a result of excitation by the primary X-rays B1. The X-ray fluorescence spectrometer of the structure described above is operable to analyze the fluorescent X-rays B3 emitted from a substance of interest present on the surface of the sample 50. The sample table 70 on which the sample 50 is placed is adapted to be driven by a driving means (not shown) so that the primary X-rays B1 can illuminate the sample 50 at an arbitrarily chosen angle of incidence and at an arbitrarily chosen position.

The X-ray source 2, the spectroscopic device 3, the sample table 70 and the driving means for the sample table 70 altogether constitute a measuring unit 5 that is operable to measure the strength of the fluorescent X-rays B3 by irradiating the standard sample and the sample to be measured with the primary X-rays B1 at a plurality of different incident angles ø1 to øn.

The X-ray fluorescence spectrometer embodying the present invention also includes a calculating means 6 operable to determine the specific glancing angles øa* and øb* (øa*<øb*) and an abundance determining unit 8 for determining the abundance of the substance of interest in the sample to be analyzed. Specifically, with respect to two glancing angles øa and øb (where øa<øb) arbitrarily chosen from the plural glancing angles measured as hereinabove described, the calculating means 6 is operable to determine the ratio between the strengths Ia1 and Ib1 of the fluorescent X-rays, emitted from the standard sample 1, as a grading coefficient PF1 and also to determine the ratio between the strengths Ia2 and Ib2 of the fluorescent X-rays, emitted from the standard sample 2, as a grading coefficient PF2 of the standard sample 2, and then to determine the corresponding specific glancing angles øa* and øb* at which the ratio of Ia2·PF1/PF2 can take a value approximating to Ia1. On the other hand, the abundance determining unit 8 is operable to determine the abundance of the substance of interest in reference to the ratio PF3 between the respective strengths Ia3 and Ib3 of the fluorescent X-rays that are emitted from samples to be analyzed when the specific glancing angles øa* and øb* so determined are employed, respectively.

The X-ray fluorescence spectrometer embodying the present invention operates in the following manner.

Where a quantitative analysis of, for example, nickel that is a contaminant to be measured present on a silicon substrate is to be carried out, total reflection X-ray fluorescence analysis (including analysis at an glancing angle of øc as will be described later) is first carried out subject to a standard sample having a known quantity of the contaminant to clarify the relationship between the amount of the contaminant and the strength of the fluorescent X-rays. In other words, a calibration curve representative of the relationship between the amount of the contaminant and the strength of the fluorescent X-rays is prepared. Subsequently, a similar total reflection fluorescent X-ray measurement is carried out subject to a sample to be measured having an unknown quantity of the contaminant to measure the strength of the fluorescent X-rays emitted from the sample to be measured. Then, using the calibration curve referred to above, the strength of the fluorescent X-rays emitted from the sample to be measured is converted into an abundance of the contaminant. In the illustrated embodiment, the substance of interest present in the standard sample 1 has a film-like distribution of the contaminant in which the contaminant is distributed on the silicon substrate in the form of a film whereas the substance of interest present in the standard sample 2 has a granular distribution of the contaminant in which the contaminant is distributed on the silicon substrate in the form of grains.

In the illustrated embodiment, the standard sample 2 having the granular distribution of the contaminant is prepared by allowing the standard sample 1 having the film-like distribution of the contaminant to stand for 30 minutes within the hydrogen fluoride atmosphere to thereby dissolve a silicon oxide film on the surface of the sample into hydrogen fluoride, then allowing the sample to stand in the atmosphere to thereby dry the solution on the silicon substrate so that the pattern of distribution of the contaminant can be transformed from the film-like distribution to the granular distribution to thereby provide the standard sample 2 having the granular distribution of the contaminant. In this case, the abundance of the contaminant does not vary.

Figure 2B:
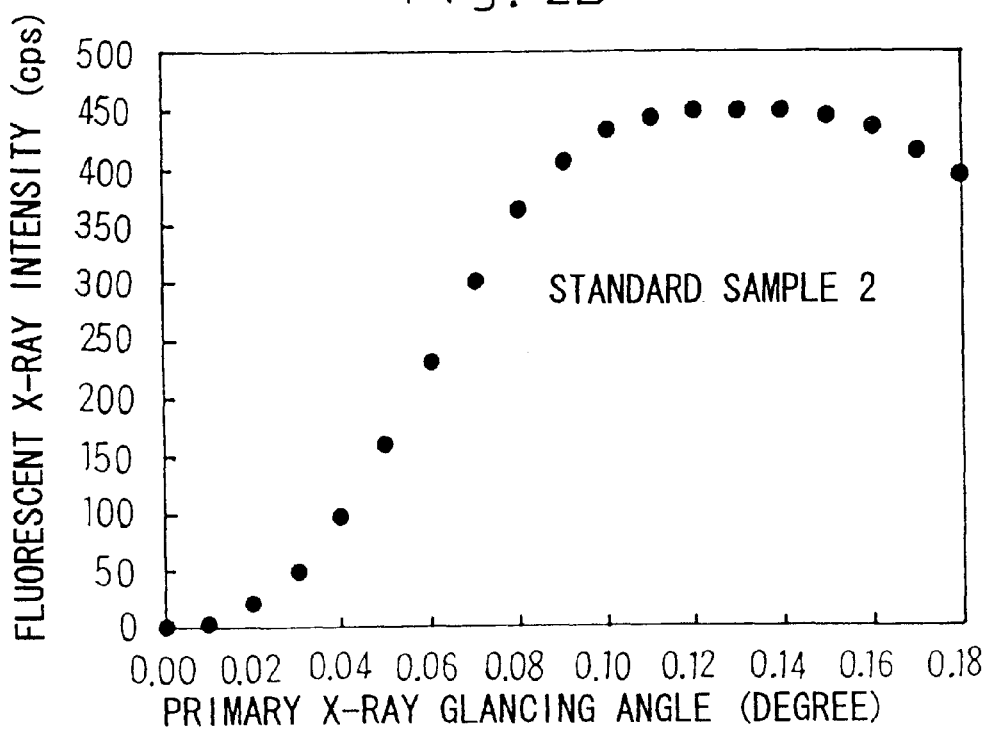
FIG. 2B is a characteristic chart showing the relationship between the strength of the fluorescent X-rays and the angle of irradiation of the primary X-rays, which is applicable where the substance of interest is distributed in the form of grains.

FIG. 2 illustrates the relationship between the strength of the fluorescent X-rays B3 emitted from the substance of interest on the surface of the silicon substrate and the glancing angle at which the primary X-rays B1 illuminate the sample. FIG. 2A is applicable where the substance of interest is distributed in the form of a film on the surface of the substrate whereas FIG. 2B is applicable where the substance of interest is distributed in the form of grains on the surface of the substrate. Comparing FIGS. 2A and 2B with each other, it will readily be seen that even though the abundance of the substance of interest remains the same, the relationship between the strength of the fluorescent X-rays B3 and the glancing angle of the primary X-rays B1 varies considerably depending on whether the substance of interest is distributed in the form of a film such as in the standard sample 1 and whether the substance of interest is distributed in the form of grains such as in the standard sample 2.

With the X-ray fluorescence spectrometer of the present invention, while the standard samples 1 and 2 are separately irradiated with the primary X-rays B1 at the different glancing angles ø1 to øn, the measuring unit 5 measures the strength of the fluorescent X-rays B3 emitted therefrom.

Hereinafter, the operation of the calculating means 6 will be described in connection with two cases 1 and 2 in which of measured data on the plural glancing angles two different glancing angles øa and øb are chosen, respectively.

Case 1, in which the glancing angles øa and øb are chosen to be 0.05 degree and 0.15 degree, respectively:

In this case, the strength of Ni-Kα lines exhibited by the standard sample 1 having the film-like distribution of the contaminant reads 20.65 cps (=Ia1) when the glancing angle øa is 0.05 degree and 335.65 cps (=Ib1) when the glancing angle øb is 0.15 degree. Accordingly, when the grading coefficient PF1 of the standard sample 1 which represents the ratio between the fluorescent X-ray strength Ia1 and Ib1 of the standard sample 1 is determined, PF1=20.65/335.65 and, hence, PF1=0.06.

On the other hand, the strength of Ni-Kα lines exhibited by the standard sample 2 having the granular distribution of the contaminant reads 158.79 cps (=Ia2) when the glancing angle øa is 0.05 degree and 444.05 cps (=Ib2) when the glancing angle øb is 0.15 degree. Accordingly, when the grading coefficient PF2 of the standard sample 2 which represents the ratio between the fluorescent X-ray strengths Ia2 and Ib2 of the standard sample 2 is determined, PF2= 158.79/444.05 and, hence, PF2=0.36. Thus, the ration PF1/PF2 equals to 0.06/0.36 and, hence, to ⅙.

At this time, the coefficient A is equal to (Ia2/Ia1)·(PF1/PF2)=(158.79/20.65)·(0.06/0.36) that is nearly equal to 1.3.

Figure 3A:
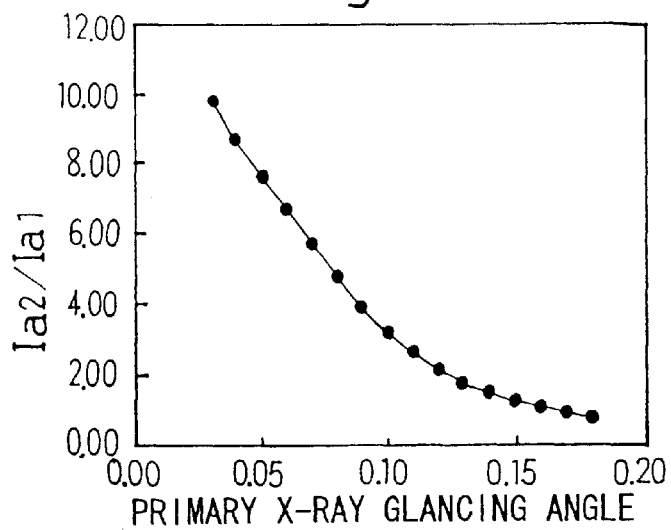
FIG. 3A is a characteristic chart showing the relationship between the angle of irradiation of the primary X-rays and the ratio between the strength of the fluorescent X-rays, emitted from a particulate standard sample, and the strength of the fluorescent X-rays emitted from a film-shaped standard sample.
Figure 3B:
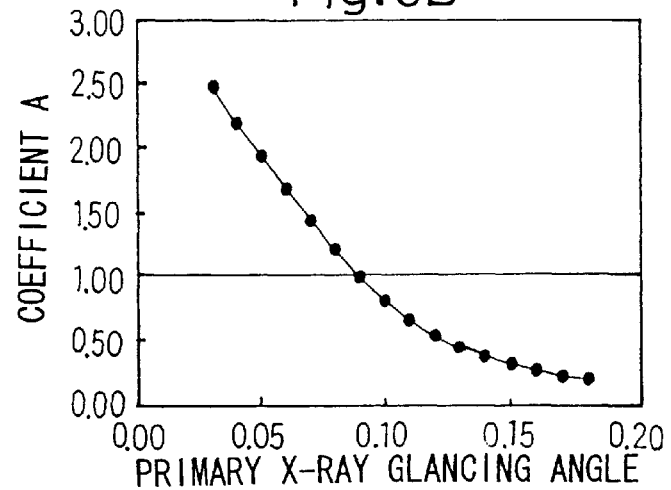
FIG. 3B is a characteristic chart showing one relationship between the angle of irradiation of the primary X-rays and the coefficient A.
Figure 3C:
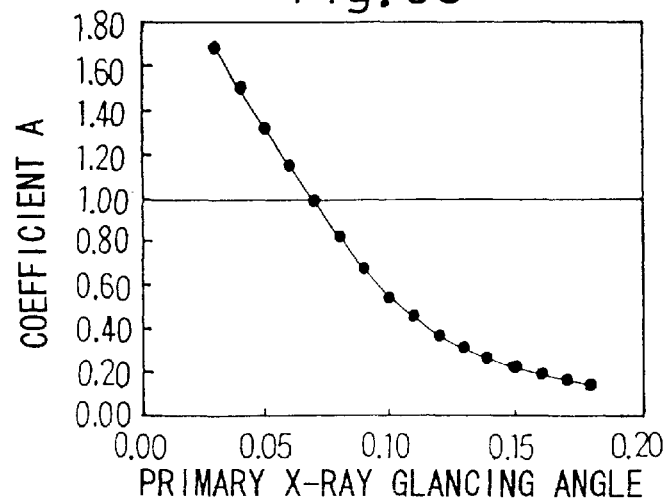
FIG. 3C is a characteristic chart showing another relationship between the angle of irradiation of the primary X-rays and the coefficient A.
Figure 4A:
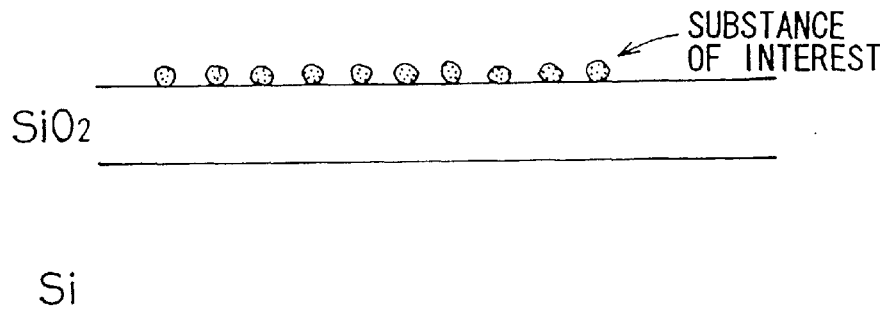
FIGS. 4A to 4C are schematic side views of a sample to be analyzed, showing different manners of distribution of substances of interest, respectively.
Figure 4B:
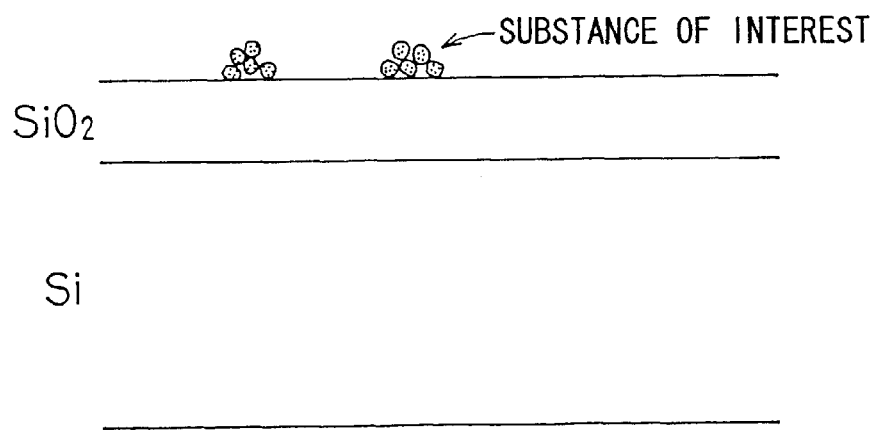
Figure 4C:
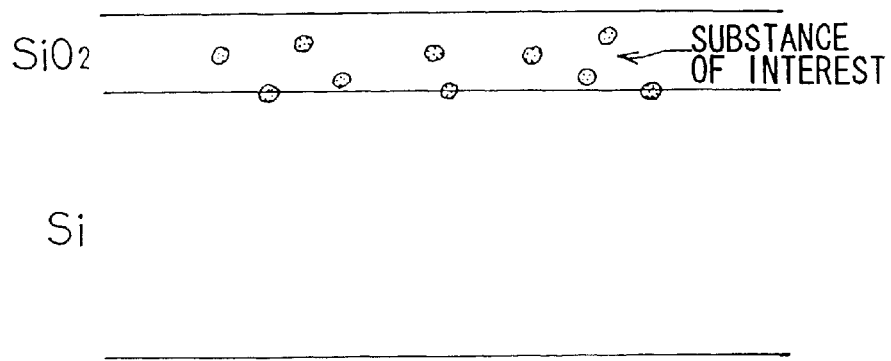

In order to provide a cue with which the coefficient A can approximate to 1, using both the PF1/PF2 so determined as hereinabove discussed and Ia2/Ia1, that is, the ratio between the fluorescent X-ray strength Ia2 of the standard sample 2 having the granular distribution of the contaminant and the fluorescent X-ray strength Ia1 of the standard sample 1 having the film-like distribution of the contaminant relative to the glancing angle of the primary X-rays B1 as shown in FIG. 3A, the relation of the coefficient A to the glancing angle of the primary X-rays B1 is plotted as shown in FIG. 3C with a view to A=(Ia2/Ia1)·(⅙). In such case, as shown in FIG. 3C, the coefficient A will be 1 in the vicinity of the glancing angle of 0.07 degree. In other words, when the calibration curve for use in the previously discussed quantitative analysis is to be prepared, it is preferred that under this condition the total reflection X-ray fluorescence analysis is carried out at the glancing angle øc=0.07 degree at which the coefficient A is nearly equal to 1.

Case 2 in which the glancing angles øa and øb are chosen to be 0.09 degree and 0.17 degree, respectively:

Even in this case, calculation similar to that described in connection with the Case 1 performed to plot the relation of the coefficient A to the glancing angle of the primary X-rays B1 as shown in FIG. 3B. As shown in FIG. 3B, the coefficient A will be 1 in the vicinity of the glancing angle of 0.09 degree. In other words, when the calibration curve for use in the previously discussed quantitative analysis is to be prepared, it is preferred that under this condition the total reflection X-ray fluorescence analysis is carried out at the glancing angle øc=0.09 degree at which the coefficient A is nearly equal to 1.

The calculating means 6 then determines as the small specific glancing angle øa*, 0.09 degree (=øc) corresponding to the coefficient A of 1 and as the large specific glancing angle øb*, for example, 0.17 degree φ(=øb) which is the larger glancing angle 0.17 degree (=øb) previously chosen. As a result of the total reflection fluorescent X-ray measurement of the standard sample 1 having the film-like distribution of the contaminant, it has been found that the strength of the Ni-Kα lines reads 103.60 cps at 0.09 degree and 419.58 cps at 0.17 degree. Accordingly, the grading coefficient PF1 of the standard sample 1 which represents the ratio between the fluorescent X-ray strengths Ia1 and Ib1 exhibited by the standard sample 1 is such that PF1=103.60/419.58=0.25. By using the calibration curve given when the irradiation angle øc is 0.09 degree the strength of the Ni-Kα lines is converted into the abundance of the contaminant Ni on the standard sample 1, giving the result of about $1.5 \times 10^{12}$ atoms/cm$^2$.

With respect to the standard sample 2 having the granular distribution of the contaminant, the strength of the Ni-Kα lines reads 404.91 cps at 0.09 degree and 415.30 cps at 0.17 degree. Accordingly, the grading coefficient PF2 of the standard sample 2 which represents the ratio between the fluorescent X-ray strengths Ia2 and Ib2 exhibited by the standard sample 2 is such that PF2=404.91/415.30=0.97. From this, the ratio between the grading coefficients PF1 and PF2 is such that PF1/PF2=0.25/0.97 that is nearly equal to ¼.

At this time, the coefficient A is equal to (Ia2/Ia1)·(PF1/PF2)=(404.91/103.60)·(0.25/0.97) that is nearly equal to 1.

In the next place, the sample to be measured in which the manner of distribution of the contaminant is unknown but the abundance thereof is the same as that of the standard sample 1 or 2 is subjected to the total reflection X-ray measurement using the specific glancing angles of øa*=0.09 degree and øb*=0.17 degree that are so determined as hereinabove discussed. In the case of the sample having the granular distribution of the contaminant, as is the case with the standard sample 2, the strengths Ia3 and Ib3 of the Ni-Kα lines read 404.91 cps at 0.09 degree and 415.30 cps at 0.17 degree. Accordingly, the grading coefficient PF3 of the sample to be measured that represents the ratio between the fluorescent X-ray strengths Ia3 and Ib3 exhibited by the sample to be measured is such as PF3=404.91/415.30=0.97. By using the calibration curve obtained at the glancing angle øc=0.09 degree, the strength of the Ni-Kα lines is converted into the abundance C1 of the contaminant Ni on the sample to be measured, giving the result of about $5.8 \times 10^{12}$ atoms/cm².

The abundance determining unit 8 makes use of the ratio PF1/PF3, that is, the ratio between the grading coefficients PF1 and PF3 (i.e., the fluorescent X-ray strength ratio) based on, for example, the grading coefficient of the standard sample 1 that is PF1=0.25 and the grading coefficient of the sample to be measured that is PF3=0.97, to perform a correction, expressed by the following equation, to the abundance C1. The abundance of the contaminant Ni after the correction is represented by C2.

$$C2 = C1 \cdot (PF1/PF3) = 5.8 \times 10^{12} \cdot (0.25/0.97) = 1.5 \times 10^{12}$$

Thus, the abundance C2 of the contaminant Ni after the correction is about $1.5 \times 10^{12}$ atoms/cm² and is hence equal to the abundance of the contaminant Ni on the standard sample 1 as hereinbefore described. Thus, it can be understood that the abundance of the substance of interest can be determined accurately.

As hereinabove described, the present invention makes it possible to determine the specific glancing angles øa* and øb* effective to render the value of Ia2·PF1/PF2 to approach the value of Ia1, that is, to enable the coefficient A to approach 1 and then to accurately determine the abundance of the substance of interest with the utilization of the ratio PF3 between the fluorescent X-ray strengths Ia3 and Ib3 that are exhibited by the sample to be measured when the latter is irradiated with the primary X-rays B1 at the specific glancing angles øa* and øb* so determined.

It is to be noted that although in the illustrated embodiment the abundance determining unit 8 has been described as operable to determine the abundance of the substance of interest based on the value ¼ of the ratio PF1/PF3 in the Case 2, the coefficient A in the Case 1 is 1.3 while the coefficient A in the Case 2 is 1 and, accordingly, the accuracy would be somewhat lowered as compared with the Case 2, but where the accuracy with the Case 1 is considered sufficient, the abundance of the substance of interest may be determined based on the value ⅙ of the ratio PF1/PF3 in the Case 1.

It is also to be noted that in the illustrated embodiment the abundance of the substance of interest has been described as determined in reference to the ratio of the fluorescent X-ray strengths exhibited by the sample to be measured, the abundance of the substance of interest may be determined based on the difference between the fluorescent X-ray strengths in a manner similar to that based on the strength ratio.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. A fluorescent X-ray analyzing method for measuring fluorescent X-rays emitted from a substance of interest present on a surface area of a sample by irradiating the surface area of the sample with primary X-rays, said method comprising:

a first step of measuring a strength of fluorescent X-rays by projecting the primary X-rays onto standard samples 1 and 2 having different distribution of the substance of interest, but having the same abundance of the substance of interest, so as to impinge thereupon at a plurality of different glancing angles of ø1 to øn;

a second step of determining a ratio between the strengths Ia1 and Ib1 of the fluorescent X-rays, emitted from the standard sample 1, for two glancing angles øa and øb (where øa<øb) arbitrarily chosen from the plural glancing angles, as a grading coefficient PF1 of the standard sample 1 and also determining a ratio between the strengths Ia2 and Ib2 of the fluorescent X-rays, emitted from the standard sample 2, for those two glancing angles øa and øb, as a grading coefficient PF2 of the standard sample 2, and then determining the corresponding specific glancing angles øa* and øb* at which the ratio of Ia2·PF1/PF2 can take a value approximating to Ia1, and a third step of determining the abundance of the substance of interest from strengths Ia3 and Ib3 of the fluorescent X-rays emitted from a sample to be measured when the latter is irradiated with the primary X-rays at respective specific glancing angles øa* and øb*.

2. The fluorescent X-ray analyzing method as claimed in claim 1, wherein the sample is a silicon substrate and the substance of interest present on the surface area of the sample is a transition metal.

3. The fluorescent X-ray analyzing method as claimed in claim 2, wherein a manner in which the substance of interest is distributed on the surface area of the sample includes a film-like distribution and a granular distribution.

4. The fluorescent X-ray analyzing method as claimed in claim 1, wherein when a coefficient A that is equal to (Ia2/Ia1)·(PF1/PF2) is within the range of 0.3 to 3, the value of Ia2·PF1/PF2 approaches the value of Ia1.

5. The fluorescent X-ray analyzing method as claimed in claim 1, wherein when a coefficient A that is equal to (Ia2/Ia1)·(PF1/PF2) is within the range of 0.8 to 1.2, the value of Ia2·PF1/PF2 approaches the value of Ia1.

6. The fluorescent X-ray analyzing method as claimed in claim 1, wherein the third step is for determining the abundance of the substance of interest from a ratio or a difference between strengths of the fluorescent X-rays emitted from the sample that are irradiated with the primary X-rays at specific glancing angles øa* and øb*, respectively.

7. The fluorescent X-ray analyzing method as claimed in claim 1, wherein the method is a total reflection fluorescent X-ray analyzing method in which the specific glancing angles øa* and øb* are minute so as to be suited for total reflection at the surface area of the sample.

8. An X-ray fluorescence spectrometer for measuring fluorescent X-rays emitted from a substance of interest present on a surface area of a sample by irradiating the surface area of the sample with primary X-rays, said spectrometer comprising:

a measuring unit for measuring a strength of fluorescent X-rays by projecting the primary X-rays onto standard samples 1 and 2 having different distribution of the substance of interest, but having the same abundance of the substance of interest, so as to impinge thereupon at a plurality of different glancing angles of ø1 to øn;

a calculating means for determining a ratio between the strengths Ia1 and Ib1 of the fluorescent X-rays, emitted from the standard sample 1, for two glancing angles øa and øb (where øa<øb) arbitrarily chosen from the plural glancing angles, as a grading coefficient PF1 of the standard sample 1 and also determining a ratio between the strengths Ia2 and Ib2 of the fluorescent X-rays, emitted from the standard sample 2, for those two glancing angles øa and øb, as a grading coefficient PF2 of the standard sample 2, and then determining the corresponding specific glancing angles øa* and øb* at which the ratio of Ia2·PF1/PF2 can take a value approximating to Ia1, and an abundance determining unit for determining the abundance of the substance of interest from strengths Ia3 and Ib3 of the fluorescent X-rays emitted from a sample to be measured when the latter is irradiated with the primary X-rays at respective specific glancing angles øa* and øb*.

9. The X-ray fluorescence spectrometer as claimed in claim 8, wherein the sample is a silicon substrate and the substance of interest present on the surface area of the sample is a transition metal.

10. The X-ray fluorescence spectrometer as claimed in claim 8, wherein a manner in which the substance of interest is distributed on the surface area of the sample includes a film-like distribution and a granular distribution.

11. The X-ray fluorescence spectrometer as claimed in claim 8, wherein when a coefficient A that is equal to (Ia2/Ia1)·(PF1/PF2) is within the range of 0.3 to 3, the value of Ia2·PF1/PF2 approaches the value of Ia1.

12. The X-ray fluorescence spectrometer as claimed in claim 8, wherein when a coefficient A that is equal to (Ia2/Ia1)·(PF1/PF2) is within the range of 0.8 to 1.2, the value of Ia2·PF1/PF2 approaches the value of Ia1.

13. The X-ray fluorescence spectrometer as claimed in claim 8, wherein the abundance determining unit is operable to determine the abundance of the substance of interest from a ratio or a difference between strengths of the fluorescent X-rays emitted from the sample that are irradiated with the primary X-rays at specific glancing angles øa* and øb*, respectively.

14. The X-ray fluorescence spectrometer as claimed in claim 8, wherein the spectrometer is a total reflection X-ray fluorescence spectrometer in which the specific glancing angles øa* and øb* are minute so as to be suited for total reflection at the surface area of the sample.

* * * * *